US00PP32969P2

(12) United States Plant Patent
Wood

(10) Patent No.: US PP32,969 P2
(45) Date of Patent: Apr. 13, 2021

(54) ***SYRINGA* PLANT NAMED 'SMNSDTP'**

(50) Latin Name: ***Syringa* hybrid**
Varietal Denomination: SMNSDTP

(71) Applicant: Spring Meadow Nursery, Inc., Grand Haven, MI (US)

(72) Inventor: Timothy D Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/879,319

(22) Filed: May 20, 2020

(51) Int. Cl.
*A01H 5/00* (2018.01)
*A01H 6/00* (2018.01)

(52) U.S. Cl.
USPC ..... Plt./248

(58) Field of Classification Search
USPC ..... Plt./226, 248
See application file for complete search history.

*Primary Examiner* — Susan McCormick Ewoldt
(74) *Attorney, Agent, or Firm* — Cassandra Bright

(57) ABSTRACT

A new and distinct variety of *Syringa* plant named 'SMNSDTP' is disclosed, characterized by a distinctive dwarf and compact plant habit. Flowers are fragrant. Flower buds are dark purple, mature flowers light lavender and white. The new variety is a *Syringa* normally produced as an outdoor garden or container plant.

3 Drawing Sheets

Latin name of the genus and species: *Syringa* hybrid.
Variety denomination: 'SMNSDTP'.

BACKGROUND OF THE INVENTION

The present invention comprises a new and distinct variety of *Syringa*, hereinafter referred to by the cultivar name 'SMNSDTP'. This new *Syringa* was developed through a breeding program in Grand Haven, Mich. The objective of the breeding program was to develop new *Syringa* reblooming varieties in different flower colors. 'SMNSDTP' is an internal advanced selection from an in-house breeding program. The seed parent is an unnamed, unpatented proprietary breeding line. The pollen parent is unidentified as the new variety was produced through an open pollination breeding program. The open pollination resulting in the new variety was made in 2005. Selection of the new variety was made during May of 2007.

The first asexual propagation of 'SMNSDTP' was carried out during June of 2007 by softwood cuttings at a commercial nursery in Grand Haven, Mich. 'SMNSDTP' has been found to retain its distinctive characteristics through successive asexual propagations. Multiple generations have been propagated, with the new variety characteristics reproduced true to type.

SUMMARY OF THE INVENTION

The following are the most outstanding and distinguishing characteristics of this new cultivar when grown under standard horticultural practices at Grand Haven, Mich.:

1. Dwarf plants.
2. Compact plant habit.
3. Strong, attractive floral fragrance.
4. Dark purple flower buds opening to distinctive light lavender and white flowers.

COMPARISON WITH THE PARENT VARIETIES

'SMNSDTP' is similar to the seed parent, in most horticultural characteristics. 'SMNSDTP' however differs in the following:

1. Plants of the new variety are smaller, more dwarf than plants of the seed parent.
2. Flowers of the new variety begin with dark purple buds, opening to light lavender and white, flower color of the seed parent are lighter purple, without dark purple bud coloration.

COMMERCIAL COMPARISON

'SMNSDTP' is similar to the commercial variety *Syringa* 'Miss Kim', unpatented, in most horticultural characteristics. 'SMNSDTP' however differs in the following:

1. Plants of the new variety are more dwarf and more compact than plants of 'Miss Kim'.
2. Flowers of the new variety begin with dark purple buds, opening to light lavender and white, flower color of 'Miss Kim' is lavender-blue.

DESCRIPTION OF THE PHOTOGRAPHS

This new *Syringa* is illustrated by the accompanying photographs which show the plant's form, foliage and inflorescences. The colors shown are as true as can be reasonably obtained by conventional photographic procedures. Plants were grown in Grand Haven, Mich.

Figure 1:
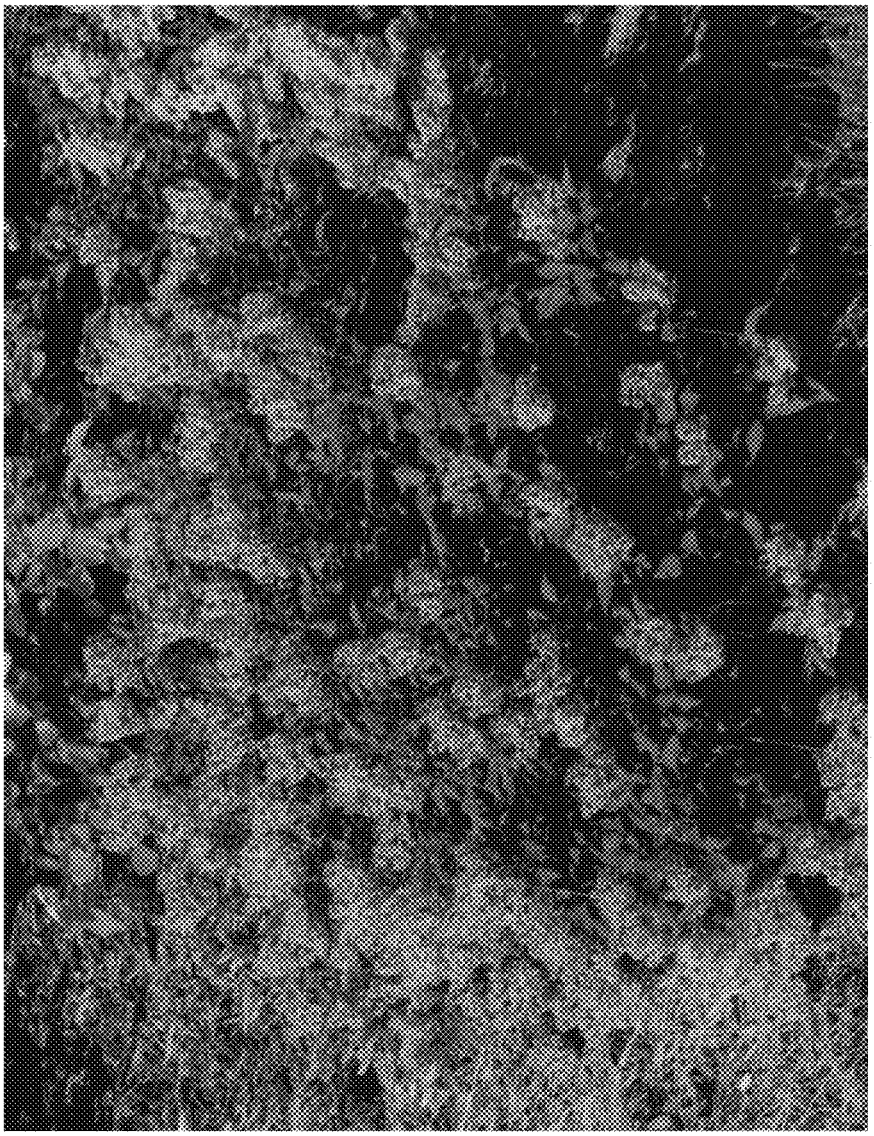

FIG. 1. shows a flowering plant of 'SMNSDTP' in the ground at approximately 3 years old during Summer.

Figure 2:
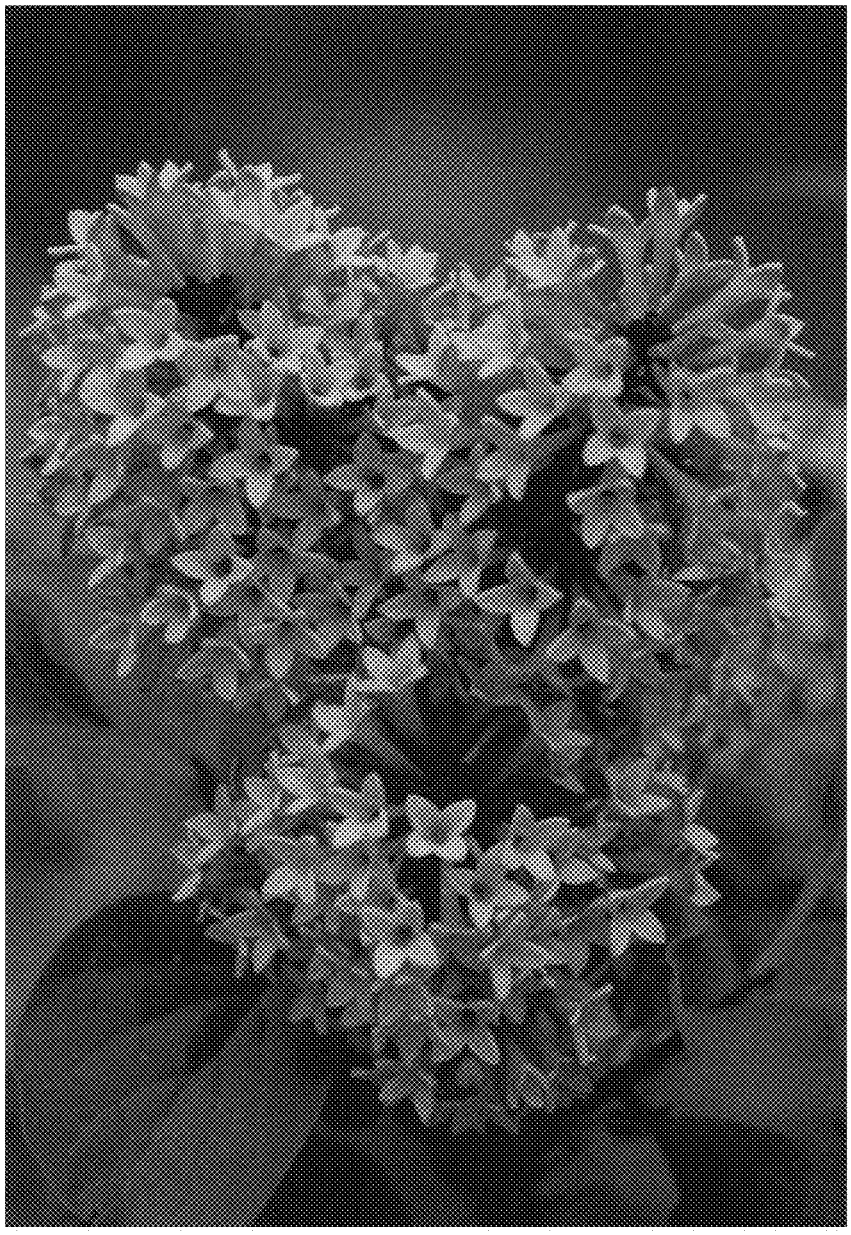

FIG. 2. shows a close-up view of the inflorescence.

Figure 3:
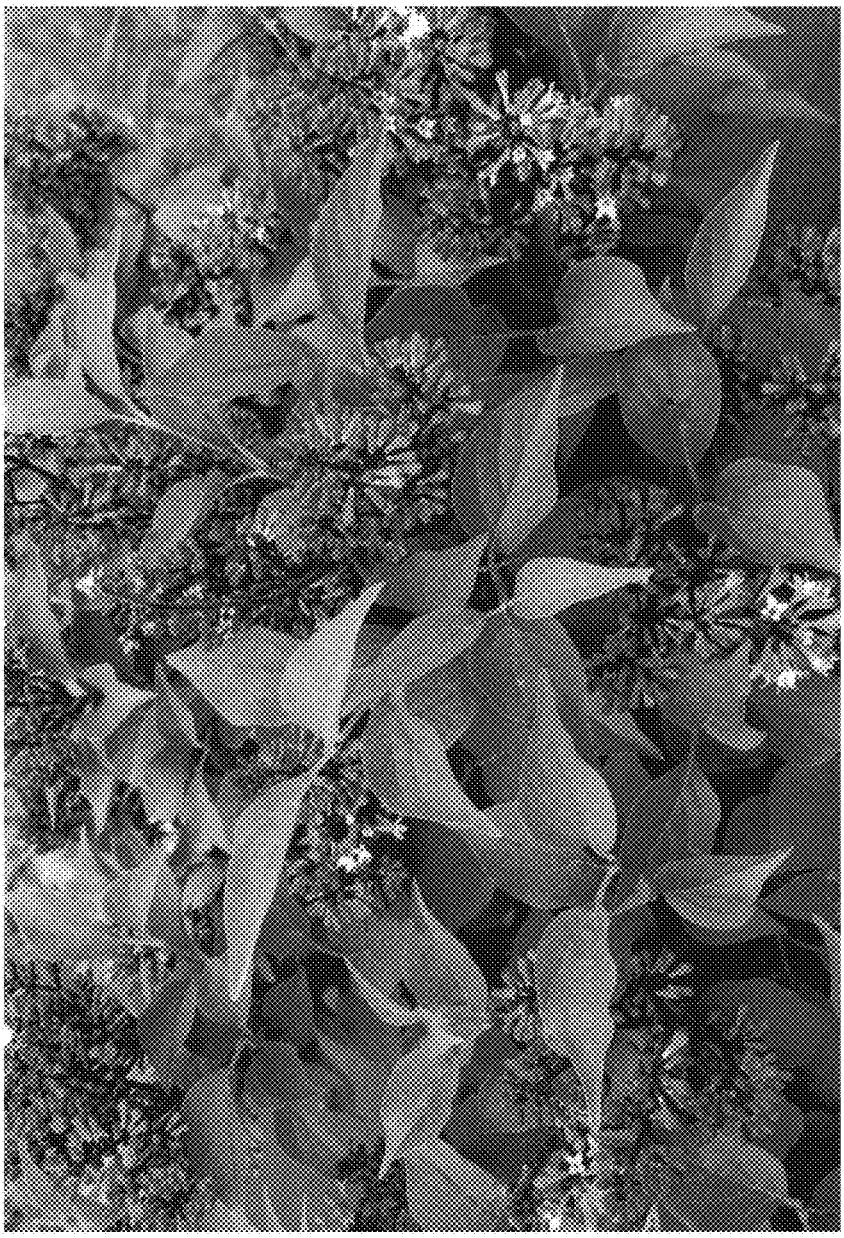

FIG. 3 illustrates a flowering plant of the new variety before flowers are fully open, illustrating bud color.

DESCRIPTION OF THE NEW CULTIVAR

In the following description, color references are made to The Royal Horticultural Society Colour Chart 2015 except where general terms of ordinary dictionary significance are used. The following observations and measurements describe 'SMNSDTP' plants grown in a poly-greenhouse during Summer, in Grand Haven, Mich. USA. The growing temperature ranged from 18° C. to 27° C. during the day and from 5° C. to 10° C. during the night. General light conditions are natural sunlight. Measurements and numerical values represent averages of typical plant types.

DETAILED BOTANICAL DESCRIPTION

Botanical classification: *Syringa* hybrid 'SMNSDTP'.
Propagation:
Typical method: Softwood cuttings.
Time to initiate rooting: About 20 days at approximately 18° C. to 27° C.
Time to produce a rooted young plant: About 3 months at approximately 18° C. to 27° C.
Root description: Dense, free branching, thin, fibrous. Colored tan, not accurately measured with an R.H.S. chart.
Plant description:
- *Age of plant described.*—About 2 years in a 3 gallon container.
- *Growth habit.*—Perennial shrub. Rounded.
- *Height.*—29 cm in a 3 gallon container.
- *Width.*—56 cm in a 3 gallon container.
- *Growth rate.*—Moderate to vigorous, until achieving dwarf mature size.
- *Typical commercial container sizes.*—2, 3, and 5 gallon.

Branches:
- *Branching habit.*—Freely branching.
- *Lateral branch quantity.*—20.
- *Lateral branch length.*—36 cm.
- *Lateral branch diameter.*—5 mm.
- *Texture.*—Glabrous.
- *Shape.*—Round.
- *Branch angle.*—0-45 degrees.
- *Branch strength.*—Strong, flexible.
- *Branch color.*—New growth: near Green 143A. Mature growth: Near Greyed-Green 197A.
- *Internode length.*—2 to 4 cm.

Foliage:
Leaves:
- *Arrangement.*—Opposite.
- *Length.*—6.5 cm.
- *Width.*—4.0 cm.
- *Shape.*—Ovate.
- *Apex.*—Acute.
- *Base.*—Obtuse.
- *Margin.*—Entire.
- *Texture upper surface.*—Glabrous.
- *Texture lower surface.*—Glabrous.
- *Color.*—Immature: Upper: Near RHS Yellow-Green 144A. Lower: Near Green 143C. Mature: Upper: Green N137A. Lower: Yellow Green 147B.

Venation:
- *Color.*—Upper: Near Yellow-Green 144C. Lower: Near Yellow-Green 144C.

Petiole:
- *Length.*—15 mm.
- *Width.*—2 mm.
- *Texture.*—Glabrous.
- *Color.*—Upper side: Near Yellow-Green 144C. Under side: Near Yellow-Green 144C.

Inflorescence:
- *Description.*—Salverform flowers arranged in panicles.
- *Flowering season.*—April to May in Grand Haven, Mich.
- *Fragrance.*—Strong, floral.
- *Number of flowers per inflorescence.*—75-100.
- *Inflorescence height.*—Average 6.5 cm.
- *Inflorescence diameter.*—Average 4.25 cm.

Flowers:
- *Flower diameter.*—7 mm.
- *Flower depth.*—1 cm.
- *Flower throat diameter.*—2 mm.
- *Flower tube diameter (base).*—1 mm.
- *Flower tube length.*—5 mm.
- *Flower angle.*—Outward.
- *Persistence.*—Self-Cleaning.

Flower bud:
- *Length.*—6 mm.
- *Diameter.*—2 mm.
- *Shape.*—Obovate.
- *Color.*—Near Purple 77A, center near 77C, base near White N155D.

Petals:
- *Number.*—4.
- *Arrangement.*—Rotate.
- *Length.*—2 mm.
- *Width.*—2 mm.
- *Shape.*—Obovate.
- *Apex.*—Acute.
- *Margin.*—Entire.
- *Texture.*—Smooth.
- *Color.*—Immature upper surface: Purple 77C, base White N155D. Immature lower surface: White N155D. Mature upper surface: Purple 77C, base White N155D. Mature lower surface: Purple 77C, base White N155D. Flower tube (interior): White N155D flushed Purple 77C. Flower throat (exterior): White N155D.

Sepals: Extremely minute (less than 1 mm by 1 mm in size) and inconspicuous.
Peduncle:
- *Length.*—1 to 3 cm.
- *Width.*—1 mm.
- *Color.*—Green 143A.
- *Texture.*—Glabrous.
- *Angle.*—About 45 degrees.
- *Strength.*—Moderate.

Pedicels:
- *Length.*—1 mm.
- *Diameter.*—1 mm.
- *Texture.*—Smooth, pubescent.
- *Color.*—Green 143A.
- *Strength.*—Good.
- *Angle.*—45 to 90 degrees.

Reproductive organs:
Gynoecium:
- *Pistil number.*—1.
- *Pistil length.*—3 mm.
- *Stigma shape.*—Oblong to rounded.
- *Stigma color.*—Close to White 155A.
- *Style length.*—About 2 mm.
- *Style color.*—Close to White 155A.

Androecium:

*Stamen number.*—2.

*Filament length.*—1.5 mm.

*Filament color.*—White N155D.

*Anther shape.*—Oblong.

*Anther length.*—2 mm.

*Anther color.*—Grey 201A.

*Amount of pollen.*—Moderate.

*Pollen color.*—Green-Yellow 1A.

OTHER CHARACTERISTICS

Fruit: Not observed to date.

Disease and insect resistance: No significant disease or pest resistance nor susceptibility have been observed.

Temperature range: Observed to tolerate temperatures between −32° C. and 36° C.

What is claimed is:

1. A new and distinct variety of *Syringa* plant named 'SMNSDTP' as illustrated and described herein.

* * * * *